US00PP25566P3

(12) United States Plant Patent
Dirr

(10) Patent No.: US PP25,566 P3
(45) Date of Patent: May 19, 2015

(54) ***HYDRANGEA MACROPHYLLA* PLANT NAMED 'PIIHM-II'**

(50) Latin Name: ***Hydrangea macrophylla* (Thunb.) Ser.**
Varietal Denomination: PIIHM-II

(71) Applicant: Michael A. Dirr, Bogart, GA (US)

(72) Inventor: Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 152 days.

(21) Appl. No.: 13/694,187

(22) Filed: Nov. 5, 2012

(65) Prior Publication Data

US 2014/0130217 P1 May 8, 2014

(51) Int. Cl.
*A01H 5/00* (2006.01)

(52) U.S. Cl.
USPC ..... Plt./250

(58) Field of Classification Search
CPC ..... A01H 5/02; A01H 5/00
USPC ..... Plt./250
See application file for complete search history.

(56) References Cited

U.S. PATENT DOCUMENTS

| | | | |
|---|---|---|---|
| PP20,176 | P3 | 7/2009 | Dirr |
| PP21,227 | P3 | 8/2010 | Dirr |
| PP23,387 | P3 | 2/2013 | Dirr |

*Primary Examiner* — June Hwu
(74) *Attorney, Agent, or Firm* — Lathrop & Gage LLP

(57) ABSTRACT

A new and distinct cultivar of *Hydrangea macrophylla* plant named 'PIIHM-II', characterized by its remontant (reblooming) trait, flowering on old wood and new growth of the season; dark pink mophead inflorescences in non-aluminum based media and violet-purple inflorescences in aluminum based media; inflorescences that age to rose-red and remain showy for an extended period of time; compact, rounded to spreading growth habit; dark green foliage; red stems; and resistance to powdery mildew.

3 Drawing Sheets

Genus and species of plant claimed: *Hydrangea macrophylla* (Thunb.) Ser.

Variety denomination: 'PIIHM-II'.

BACKGROUND OF THE INVENTION

The present invention relates to a new and distinct cultivar of *Hydrangea macrophylla,* a member of the Hydrangeaceae family, hereinafter referred to by its cultivar name 'PIIHM-II'. This cultivar is grown primarily as an ornamental for landscape use and for use as a potted plant. The cultivar originated from an open pollination of *Hydrangea macrophylla* 'PIIHM-I' (U.S. Plant Pat. No. 20,176) in Watkinsville, Ga. in 2009, and was selected from the progeny by continued evaluation for growth habit, floral, and foliage characteristics.

'PIIHM-II' has been asexually reproduced by softwood cuttings since 2009 in Watkinsville, Ga. The characteristics of the cultivar have been stable and reproduced true to type in successive vegetative generations.

SUMMARY OF THE INVENTION

'PIIHM-II' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIHM-II' from all other varieties in commerce known to the inventor.

1) Remontant (reblooming) trait, flowering on old wood and new growth of the season.
2) Dark pink mophead inflorescences in non-aluminum based media and violet-purple inflorescences in aluminum based media.
3) Inflorescences that age to rose-red and remain showy for an extended period of time.
4) Compact, rounded to spreading growth habit.
5) Dark green foliage.
6) Red stems.
7) Resistance to powdery mildew.

'PIIHM-II' is distinguished from its female parent 'PIIHM-I' by its inflorescence type, flower color, foliage color, stem color, and its growth habit. 'PIIHM-II' has dark pink mophead inflorescences in non-aluminum based media and violet-purple inflorescences in aluminum based media, whereas 'PIIHM-I' has bright pink lacecap inflorescences in non-aluminum based media and pink-purple inflorescences in aluminum based media. 'PIIHM-II' has thicker, darker green leaves than 'PIIHM-I'. 'PIIHM-II' has red stems, whereas 'PIIHM-I' has pink-red stems. 'PIIHM-II' has a more compact growth habit than 'PIIHM-I'. There are no other cultivars of *Hydrangea macrophylla* with this combination of traits known to the inventor.

'PIIHM-II' can be compared to the cultivar 'After Midnight' (not patented) but differs in the following characteristics. 'PIIHM-II' reblooms throughout the growing season, whereas 'After Midnight' does not. 'PIIHM-II' has richer and darker flower color than 'After Midnight'. 'PIIHM-II' has improved resistance to powdery mildew compared to 'After Midnight'.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

DETAILED DESCRIPTION

Figure 1:
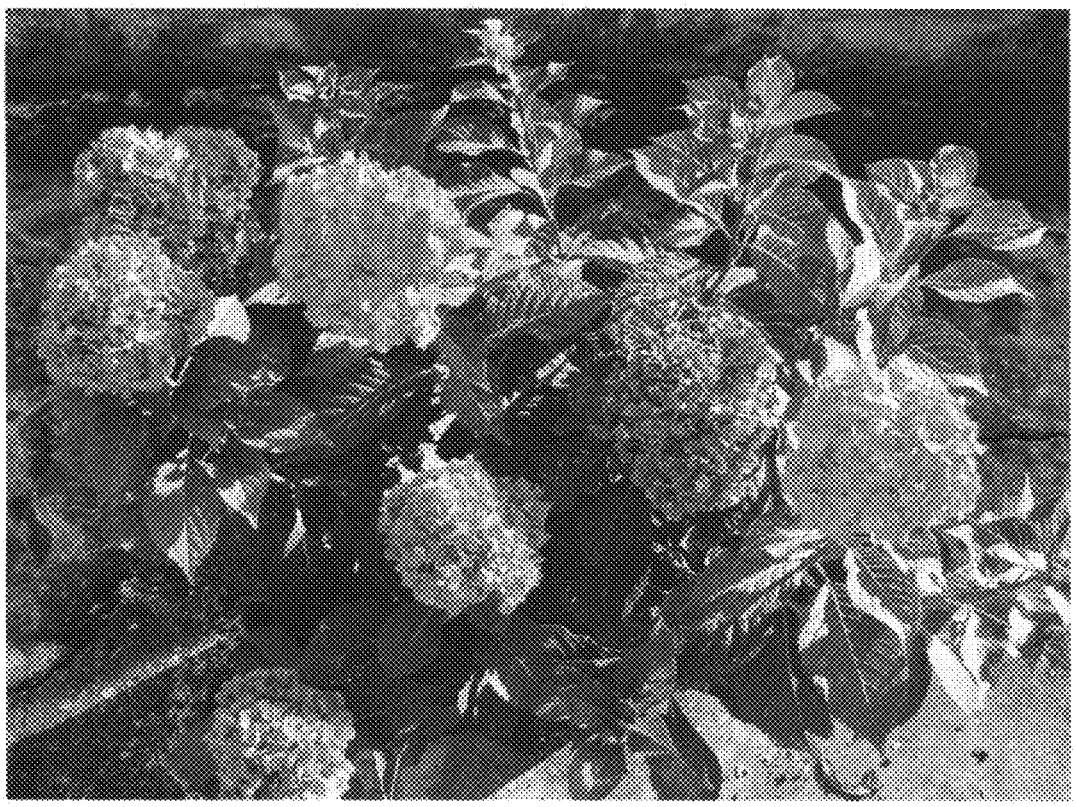
FIG. 1 shows a two-year-old 'PIIHM-II' plant grown without aluminum with mature and aged inflorescences.
Figure 2:
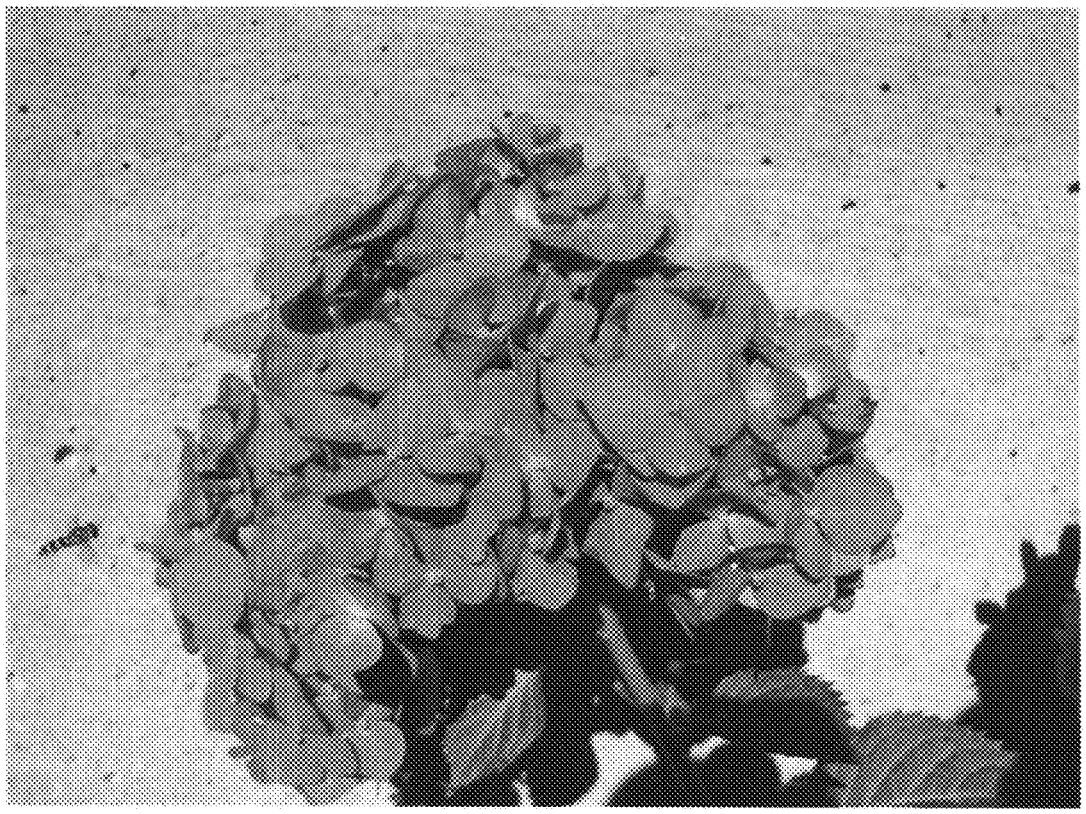
FIG. 2 shows an inflorescence on a two-year-old 'PIIHM-II' plant growing with aluminum.
Figure 3:
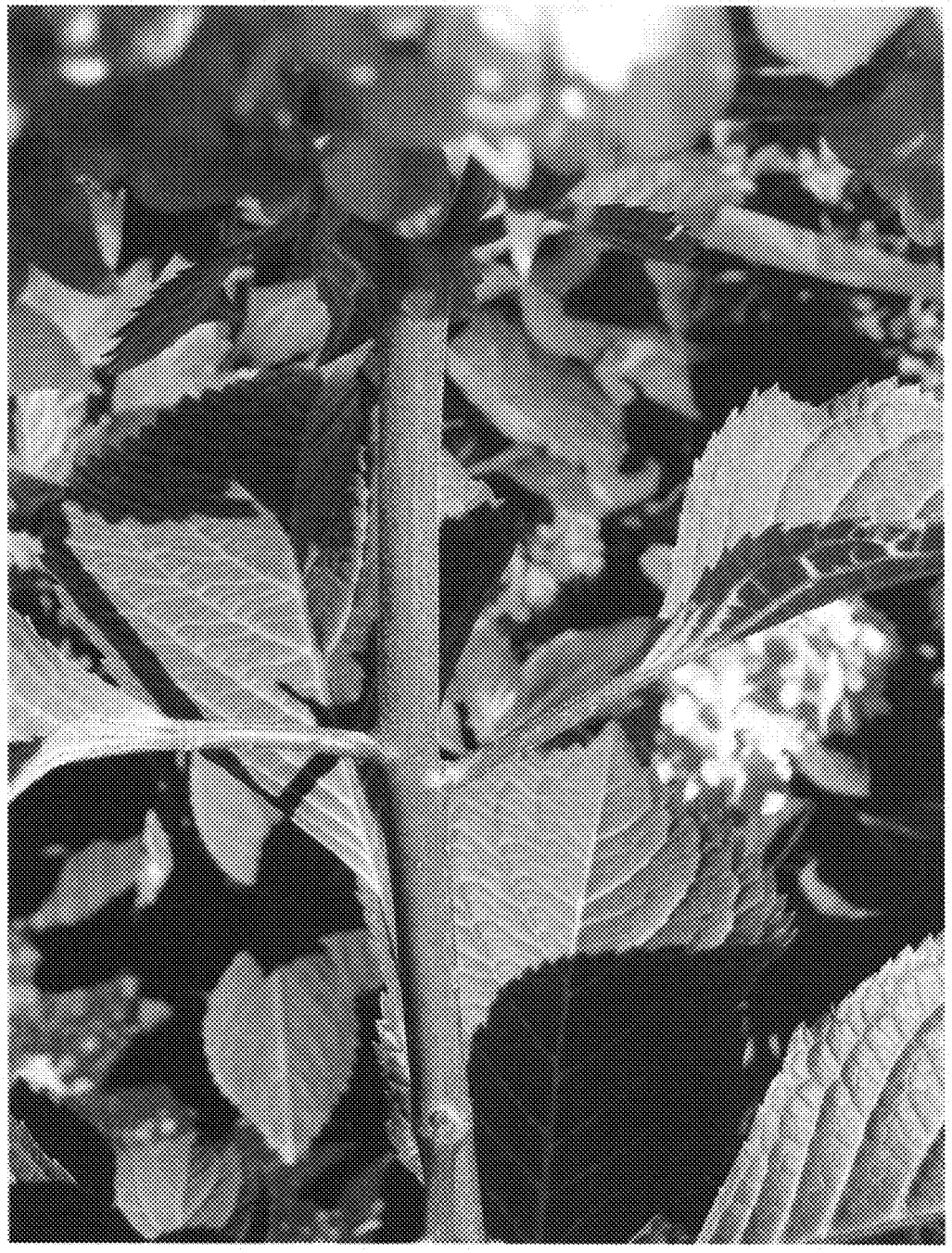
FIG. 3 shows a close up of a stem and mature foliage of a two-year-old 'PIIHM-II' plant in summer.

In the following description, color references are made to The Royal Horticultural Society Colour Chart, 2007 Edition, except where general terms of ordinary dictionary significance are used. Plants used for the description were grown in 11.8 L containers under 50% shade under outdoor conditions in a nursery in Watkinsville, Ga. Plants were about 2 years old when the description was recorded. Two groups of plants were used for the description to describe the flower colors with and without aluminum. The first group was grown in a medium consisting of composted pine bark, with no aluminum present and a pH of 5.7. The second group was grown in a medium consisting of composted pine bark that was amended with 45 grams of aluminum sulphate and a pH of 5.7. Aluminum only affects flower color. Therefore, colors with and without aluminum are only specified for floral parts.

Botanical classification: 'PIIHM-II' is a cultivar of *Hydrangea macrophylla*.

Parentage: The current variety is a progeny from an open pollination of *Hydrangea macrophylla* 'PIIHM-I' (U.S. Plant Pat. No. 20,176).

Propagation: Vegetatively by stem cuttings.

Plant description: The claimed variety is a compact, rounded and spreading deciduous shrub. The original plant, now about 4-years-old in the ground, is about 91 cm in height from the soil level to the top of the inflorescences, and about 109 cm in diameter. Freely branching. The plant is cold hardy in USDA Zones 5 to 9.

*Stems*.—First year stems have a diameter of about 4 mm, a round shape, and a stout and lustrous texture with very fine pubescence.

*Exfoliation*.—On second year and older stems, flaky and stringy, color 161A. Internodes have a length of about 4.1 cm. The stem color is 178A. Second year stems have a diameter of about 6 mm or more and are N199D in color.

*Vegetative buds*.—Arrangement: opposite. Shape: Ovoid. Size: About 2 mm in length, about 1 mm in width. Color: 178A.

Leaves:

*Size*.—About 10 cm in length and about 5.9 cm in width.

*Shape*.—Ovate, with acuminate apex, cuneate base and serrate margin.

*Texture*.—Upper surface is thick and leathery covered with a fine pubescence, 155A in color; lower surface is thick and leathery with tuffs of pubescence, 155A in color, in the axils of the secondary veins.

*Color*.—Emerging leaves are 139A on the upper surface and 147B on the lower surface; mature leaves on the upper surface are 147A, and 147B on the lower surface.

*Winter leaf color*.—On the upper and lower surface 53C.

*Venation*.—Pinnate, veins are 182A at the base of the leaf changing to 146D in color on the majority of the upper and lower surfaces.

*Petiole*.—About 1.3 cm in length and about 2.5 mm in diameter, upper and lower surface smooth and glabrous, and 183B in color. Petiole is grooved on upper side and crescent-shaped in cross section.

Flowers:

*Inflorescence bloom period*.—Early summer to first frost in fall. An inflorescence contains about 68 individual fertile flowers. An inflorescence contains about 443 individual sterile florets.

*Inflorescence shape and size*.—Mophead, about 7.5 cm in height and about 13 cm in diameter. The inflorescence is effective for about 8 weeks. The peduncle is about 5.1 cm in length, is finely pubescent, and is N77D in color with aluminum and 61B in color without aluminum. The pedicels are about 1.2 cm in length, finely pubescent, and N77D in color with aluminum and 61B in color without aluminum.

*Flower bud size*.—About 2 mm in length, about 2 mm in diameter.

*Flower bud shape*.—Round.

*Color*.—86B when grown with aluminum, and N74C when grown without aluminum.

*Sterile florets*.—Are about 2.1 cm in diameter. Each floret contains 4 sepals about 1 cm in length and about 9 mm in width. Sterile floret shape: Ovoid with obtuse apex, acute base, and entire margin. Texture: Smooth with no pubescence. Color at maturity: With aluminum, the upper surface is N82A and the lower surface is N82C. Without aluminum, the upper surface is 71B and lower surface is N74D. Color of aged sepals: With aluminum, the upper and lower surfaces are 185B. Without aluminum, the upper and lower surfaces are 184C.

*Petals (fertile flowers)*.—Size: 5 petals per flower, about 3 mm in length and about 1.5 mm in width. Shape: Ovate, with acuminate apex, truncate base, and entire margin. Texture: Smooth with no pubescence. Color: At peak of bloom the upper surface of the petals is N88A and the lower surface is N88B with aluminum. When grown without aluminum the upper surface of the petals is N74C and the lower surface is N74D.

*Sepals*.—5 per flower, 1.5 mm in length and 0.75 mm in width. Color of sepal: On upper and lower surface with aluminum N88B. Color of sepal: On upper and lower surface 62B without aluminum.

*Number of stamens*.—6 to 10.

*Anthers*.—About 1 mm in length and about 0.5 mm in width. N88A in color with aluminum and N80B in color without aluminum.

*Filaments*.—About 3 mm in length and N88B in color with aluminum and N80A in color without aluminum.

*Pollen*.—155D in color, produced in moderate quantities.

*Pistil*.—Superior, about 3 mm in length and about 1.5 mm in width, N88A in color with aluminum and N74B in color without aluminum.

*Stigma*.—Usually 2 but sometimes 3 per pistil, round in shape and N88B in color with aluminum and 76A in color without aluminum.

*Style*.—About 2 mm in length and tubular in shape, N88A in color with aluminum and 71D in color without aluminum.

Fruit: The capsule fruit is ovoid, about 3 mm in length and about 2 mm in width. The color during early ripening is close to 54B and at maturity is close to 200C. The number of fruit per infructescence varies widely.

*Seed*.—The seeds are round, about 0.5 mm in length and about 0.5 mm in width, close to 199B, and each capsule contains about 50 seeds.

Plant hardiness:

*Plant hardiness*.—USDA Plant Hardiness Zone Map (2012): Zone 5 to 9.

Disease/pest resistance: Resistant to powdery mildew. No other pest or disease resistance/susceptibility has been observed.

I claim:

1. A new and distinct *Hydrangea macrophylla* plant named 'PIIHM-II', substantially as illustrated and described herein.

* * * * *